United States Patent
Snopek et al.

(10) Patent No.: US 12,205,134 B2
(45) Date of Patent: *Jan. 21, 2025

(54) SYSTEMS AND METHODS FOR AUTONOMOUS MANAGEMENT OF MANUFACTURER COUPONS

(71) Applicant: WALGREEN CO., Deerfield, IL (US)

(72) Inventors: Adam Robert Snopek, Chicago, IL (US); Renata Lurye, Glenview, IL (US); Oliver Derza, Willowbrook, IL (US)

(73) Assignee: WALGREEN CO., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/196,802

(22) Filed: May 12, 2023

(65) Prior Publication Data

US 2023/0281654 A1 Sep. 7, 2023

Related U.S. Application Data

(63) Continuation of application No. 16/596,179, filed on Oct. 8, 2019, now Pat. No. 11,790,389.

(51) Int. Cl.
| | |
|---|---|
| G06Q 30/00 | (2023.01) |
| G06F 16/951 | (2019.01) |
| G06Q 30/0207 | (2023.01) |
| G06Q 30/0226 | (2023.01) |
| G06Q 30/0238 | (2023.01) |
| G16H 20/10 | (2018.01) |

(52) U.S. Cl.
CPC ....... *G06Q 30/0232* (2013.01); *G06F 16/951* (2019.01); *G06Q 30/0224* (2013.01); *G06Q 30/0238* (2013.01); *G16H 20/10* (2018.01)

(58) Field of Classification Search
CPC .......... G06Q 30/0232; G06Q 30/0224; G06Q 30/0238; G06F 16/951; G16H 20/10
USPC ...................................................... 705/14.32
See application file for complete search history.

(56) References Cited

U.S. PATENT DOCUMENTS

| | | | |
|---|---|---|---|
| 2004/0030598 A1* | 2/2004 | Boal ................. | G06Q 30/0235 705/14.66 |
| 2004/0125755 A1 | 7/2004 | Roberts | |
| 2008/0205850 A1* | 8/2008 | Collins .............. | G06Q 30/0241 386/E5.034 |
| 2009/0283589 A1* | 11/2009 | Moore ................ | H04L 9/3234 235/382 |

(Continued)

OTHER PUBLICATIONS

Y. Wan and G. Peng, "What's Next for Shopbots?," in Computer, vol. 43, No. 5, pp. 20-26, May 2010, doi: 10.1109/MC.2010.93. (Year: 2010).*

(Continued)

*Primary Examiner* — Sun M Li
(74) *Attorney, Agent, or Firm* — MARSHALL, GERSTEIN & BORUN LLP

(57) ABSTRACT

Methods and systems may support dynamic, real-time or near-real-time processing, analysis, and processing of data to automatically identify and obtain coupons corresponding to consumer products such that, in response to receiving a request to purchase one or more products, qualifying coupons may be automatically identified, retrieved, and applied to the purchase.

20 Claims, 6 Drawing Sheets

(56) References Cited

U.S. PATENT DOCUMENTS

| | | | | |
|---|---|---|---|---|
| 2011/0106605 | A1* | 5/2011 | Malik | G06Q 30/0224 |
| | | | | 705/14.23 |
| 2012/0136712 | A1* | 5/2012 | Chang | G06Q 20/20 |
| | | | | 705/14.38 |
| 2013/0290172 | A1* | 10/2013 | Mashinsky | G06Q 20/28 |
| | | | | 705/39 |
| 2016/0300256 | A1* | 10/2016 | Nagarajan | G06Q 30/02 |
| 2019/0214116 | A1* | 7/2019 | Eberting | G16H 40/20 |

OTHER PUBLICATIONS

Removable Anti-coupon Bar code for Confirming Consumer Attention An IP.com Prior Art Database Technical Disclosure Authors et. al.: Disclosed Anonymously IP.com No. IPCOM000197125D IP.com Electronic Publication Date: Jun. 23, 2010 (Year: 2010).*

Y. Wan and G. Peng, "What's Next for Shopbots?," in Computer, vol. 43, No. 5, pp. 20-26, May 2010, doi: 10.1109/MC.2010.93. (Year: 2010) (Year: 2010).*

M. Chevalier, J. Mothe and P. Terrier, "Tags and Information Recollection," 2016 12th International Conference on Signal-Image Technology & Internet-Based Systems (SITIS), Naples, Italy, 2016, pp. 373-380, doi: 10.1109/SITIS.2016.66. (Year: 2016 (Year: 2016).*

Chevalier et al., "Tags and Information Recollection," 2016 12th International Conference on Signal-Image Technology & Internet-Based Systems (SITIS), Naples, Italy, 2016, pp. 373-380, doi: 10.1109/SITIS.2016.66. (Year: 2016).

Wan et al., "What's Next for Shopbots?," in Computer, vol. 43, No. 5, pp. 20-26, May 2010, doi: 10.1109/MC.2010.93. (Year: 2010).

Paulson et al., "Scanning the Future with New Barcodes," in Computer, vol. 44, No. 1, pp. 20-23, Jan. 2011, doi: 10.1109/MC.2011.25. (Year: 2011).

Javkar et al., "Best offer recommendation service," 2016 International Conference on Advances in Computing, Communications and Informatics (ICACCI), 2016, pp. 2430-2436, doi: 10.1109/ICACCI.2016.7732421. (Year: 2016).

* cited by examiner

SYSTEMS AND METHODS FOR AUTONOMOUS MANAGEMENT OF MANUFACTURER COUPONS

CROSS-REFERENCE TO RELATED APPLICATIONS

This application claims priority to, and the benefit of the filing date of, U.S. patent application Ser. No. 16/596,179, filed Oct. 8, 2019 and entitled "SYSTEMS AND METHODS FOR AUTONOMOUS MANAGEMENT OF MANUFACTURER COUPONS," the entirety of the disclosure of which is hereby incorporated by reference.

FIELD OF DISCLOSURE

The present disclosure generally relates to systems and methods for autonomously monitoring the availability and application of third-party coupons toward a purchase.

BACKGROUND

The high cost of prescription medication has become increasingly problematic for many individuals. While medical insurance can decrease costs, many individuals still feel the substantial financial strain of out of pocket expenses. Additionally, with coverage varying based on insurance provider and/or many prescription medications not being covered by any provider, there exists significant cost uncertainty with prescription medications. Furthermore, many individuals are unable to even afford insurance. Consequently, many individuals forgo obtaining necessary medical treatment because they cannot afford the costs of medication. However, the existence of a financial incentive can affect a consumer's choice and/or willingness to purchase a product.

While some retailers and/or manufacturers offer incentives such as coupons to help induce sales and/or defray the costs of prescription medication, many consumers and retailers are unaware such coupons exist and do not know how to go about obtaining such coupons. Those who are aware of such coupons typically have to spend time and effort looking through magazines and advertisements to clip coupons, or search the internet and divulge sensitive information. Not to mention, applicable coupons may be offered through mediums that do not necessarily reach all customers. For example, a manufacturer may provide a coupon for a prescription medication in a monthly edition of a golf magazine, however the magazine may not be subscribed to or viewed by a large population of the medication's users. Once the consumer has successfully obtained a coupon, in some circumstances, this then requires the customer to remember to bring the coupon to the retailer at the time of purchasing the item. Whereas in other circumstances, redeeming the coupon may require additional effort from the customer to mail-in the coupon with a proof of purchase, and then wait several weeks or months to receive reimbursement. Some individuals are aware of available and applicable coupons, but are nevertheless self-conscious or embarrassed to use publically use coupons.

While consumers may apply a coupon for a discount from the retailer, this can result in losses for the retailer because the retailer may not be reimbursed by the manufacturer if the customer was not eligible to use the coupon, if the purchased product was not covered by the coupon, if the retailer erroneously accepted an expired coupon, if the retailer misplaced the coupon before sending it to the manufacturers, or if various other issues arise. Similarly, the consumer may purchase or attempt to purchase a product under the belief that the cost will be partially or fully subsidized, only to later discover that the coupon cannot be applied because he/she is not eligible and/or the product is not covered by the coupon.

Consumers also unknowingly pay full price or purchase a product for which there is a suitable alternative that is less money and/or is eligible for a coupon. However, in such situations, especially within the prescription medication industry, the typical consumer lacks the specialized knowledge required to identify acceptable/suitable replacements. Therefore, a consumer cannot effectively monitor the marketplace for all applicable coupons that may influence his/her product selection.

Accordingly, there exists a need to better facilitate the use of coupons among manufacturers, retailers, and consumers, particularly among the various computing systems by which coupons may be provided and applied.

SUMMARY

At a high level, methods and systems described herein may support dynamic, real-time or near-real-time processing, analysis, and processing of data to automatically identify and obtain coupons corresponding to consumer products such that, in response to receiving a request to purchase one or more products, qualifying coupons may be automatically identified, retrieved, and applied to the purchase.

In one embodiment, a computing system is provided. The computing system may include one or more processors and one or more computer memories storing non-transitory computer-executable instructions that, when executed via the one or more processors, cause the computing system to (1) transmit a request for a server to generate and provide one or more available coupons as a portable document format (PDF) file or webpage representing the one or more available coupons, (2) obtain the generated PDF or webpage from the third-party server, (3) extract relevant coupon data for the one or more available coupons from the obtained PDF or webpage at least by (i) identifying an electronic file format of the obtained PDF or webpage, (ii) standardizing or resizing the downloaded PDF or webpage based upon a pixel width of the downloaded PDF or webpage, (iii) determining a location of a bounding box containing the relevant coupon data within the standardized or resized PDF or webpage, and (iv) applying an optical character recognition technique within the determined bounding box to identify text corresponding to the relevant coupon data, and/or (4) using the extracted relevant coupon data, apply the one or more available coupons in relation to a purchase of one or more products. The computing system may include additional, fewer, or alternate components, and/or may perform additional, fewer, or alternate actions, as described herein.

In another embodiment, a computer-implemented is provided, the method being implemented via one or more processors. The method may include (1) transmitting a request for a server to generate and provide one or more available coupons as a portable document format (PDF) file or webpage representing the one or more available coupons, (2) obtaining the generated PDF or webpage from the third-party server, (3) extract relevant coupon data for the one or more available coupons from the obtained PDF or webpage at least by (i) identifying an electronic file format of the obtained PDF or webpage, (ii) standardizing or resizing the downloaded PDF or webpage based upon a pixel width of the downloaded PDF or webpage, (iii) determining a location of a bounding box containing the relevant coupon data within the standardized or resized PDF or webpage, and (iv) applying an optical character recognition technique within the determined bounding box to identify text corresponding to the relevant coupon data, and/or (4) using the extracted relevant coupon data, applying the one or more available coupons in relation to a purchase of one or more products. The method may include additional, fewer, and/or alternate actions, including actions described herein.

In another embodiment, one or more non-transitory computer-readable media are provided. The one or more non-transitory computer-readable media may store non-transitory computer-executable instructions that, when executed via one or more processors of one or more computers, cause the one or more computers to (1) transmit a request for a server to generate and provide one or more available coupons as a portable document format (PDF) file or webpage representing the one or more available coupons, (2) obtain the generated PDF or webpage from the third-party server, (3) extract relevant coupon data for the one or more available coupons from the obtained PDF or webpage at least by (i) identifying an electronic file format of the obtained PDF or webpage, (ii) standardizing or resizing the downloaded PDF or webpage based upon a pixel width of the downloaded PDF or webpage, (iii) determining a location of a bounding box containing the relevant coupon data within the standardized or resized PDF or webpage, and (iv) applying an optical character recognition technique within the determined bounding box to identify text corresponding to the relevant coupon data, and/or (4) using the extracted relevant coupon data, apply the one or more available coupons in relation to a purchase of one or more products. The one or more non-transitory computer-readable media may store additional, fewer, or alternate instructions, including instructions described herein.

BRIEF DESCRIPTION OF THE DRAWINGS

The figures described below depict various aspects of the systems and methods disclosed herein. Advantages will become more apparent to those skilled in the art from the following description of the preferred embodiments which have been shown and described by way of illustration. The present embodiments may be capable of other and different embodiments, and their details are capable of modification in various respects. Accordingly, the drawings and description are to be regarded as illustrative in nature and not as restrictive. Further, wherever possible, the following description refers to the reference numerals included in the following figures, in which features depicted in multiple figures are designated with consistent reference numerals.

DETAILED DESCRIPTION

The present disclosure generally relates to a system and method for determining available coupons and obtaining an available coupon to apply toward the purchase of a consumer good or service. According to implementations, the systems and methods may support a dynamic, real-time or near-real-time processing, analysis, and processing of data to automatically determine one or more available coupons, obtain one or more coupons, and apply the obtained one or more coupons toward the purchase of a consumer good or service.

As used herein, the term "coupon" may refer to any promotion, savings, discount, voucher, rebate, ticket, etc. that can be redeemed for or applied toward the purchase of one or more consumer goods or services (collectively referred to herein as "product"). Such coupon may be a price reduction (e.g., $5 off the purchase of a specific product), for a free trail (e.g., coupon redeemable in exchange for a free month's trial of a prescription drug). A coupon may include a physical article (e.g., a piece of paper), a virtual/digital depiction (e.g., an image on a computer screen), a string of characters, and/or any other suitable digital or physical material. A coupon may be offered, provided, issued or otherwise made available by a business (e.g., a retail merchant, pharmacy, service business, etc.) who sells a product or offers a service, a manufacturer who manufacturers/produces the product, or another party (e.g., a food manufacturing company offering a coupon for a movie ticket as part of a cross-promotion). Such businesses or manufacturers are generally referred to herein as "third-parties").

As used herein, the term "product" may refer to any consumer/commercially available good or service that is offered for sale. While the terms "products and services" may be used in conjunction in some parts of this disclosure, it should be appreciated that as used herein the term "product" is intended to also encompass commercially available services. Accordingly, any disclosure only describing product is for brevity purposes.

As used herein, the term "order" refers to a submission of a request to purchase, fill, refill, schedule, or otherwise be supplied with one or more products. As described herein, an order may generally be provided via a "customer" (or "consumer"), who may provide the order via a personal client devices and/or other computing devices and techniques described herein.

I. Example Computing Environment

Figure 1:
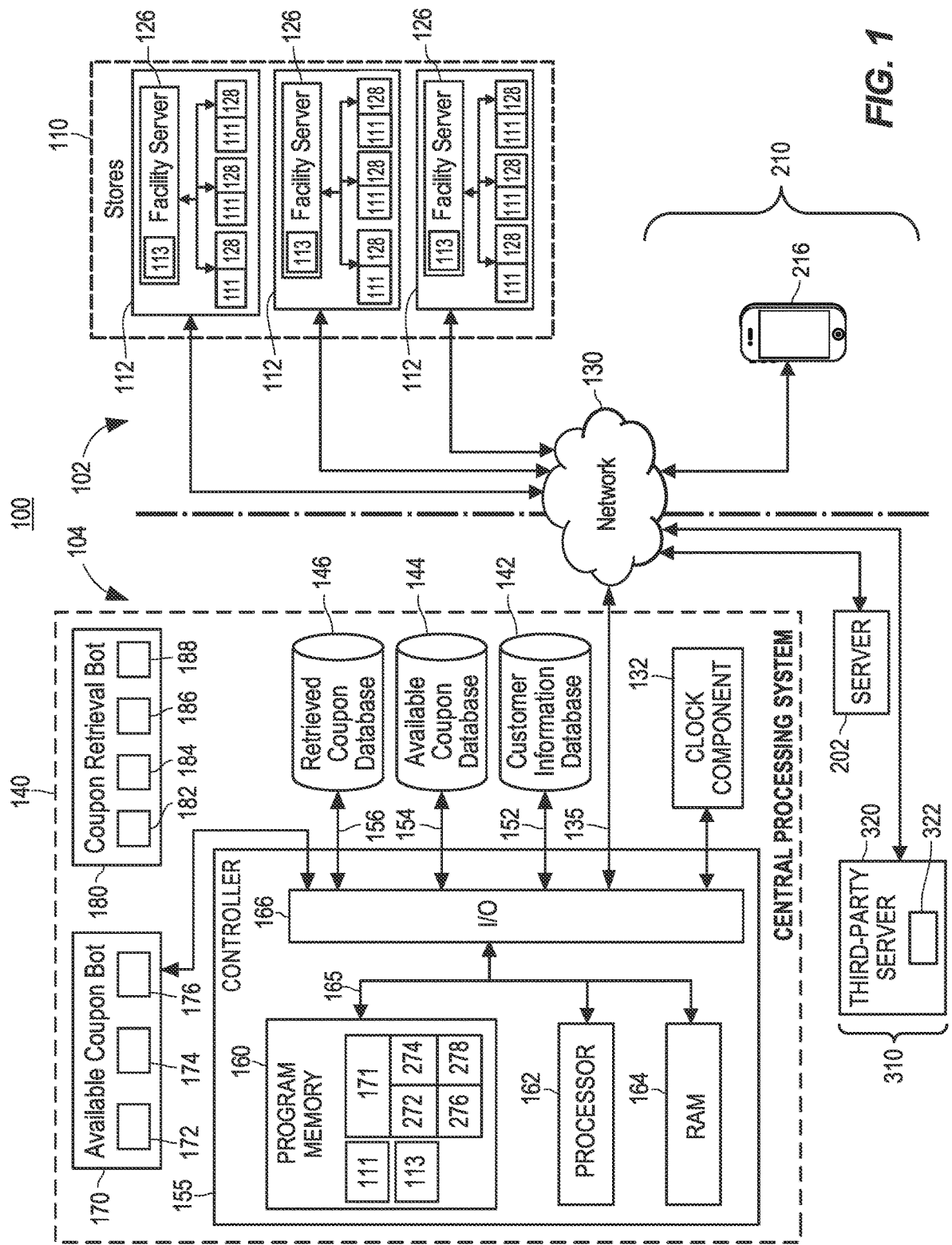
FIG. 1 illustrates a block diagram of a system for managing coupons, in accordance with some embodiments.

FIG. 1 illustrates a block diagram of an example computing environment ("system") 100 for managing coupons. It should be appreciated that the system 100 is merely an example and that alternative or additional components are envisioned.

The system 100 includes both hardware and software applications, as well as various data communication channels for communicating data between the various hardware and software components. The system 100 may be roughly divided into front-end components 102 and back-end components 104. The front-end components may include a retail host network 110 and/or a client network 210. The back-end components may include a central processing system 140, one or more enterprise proprietary servers 202, and/or a third-party network 310.

The front-end components 102 communicate with the back-end components 104 via a digital network 130 (i.e., one or more networks). The digital network 130 may include a proprietary network, a secure public Internet, a virtual private network, and/or some other type of network (e.g., dedicated access lines, plain ordinary telephone lines, satellite links, combinations of these, etc.). In embodiments in which the digital network 130 comprises the Internet, data communication may take place over the digital network 130 via an Internet communication protocol.

The front-end components 102 may be at least partially disposed within a retail host network 110, which may one or more retail stores 112. Additionally or alternatively, the front-end components 102 may be at least partially disposed within a client network 210, including one or more client devices and/or any physical environment in which a user is physically present. In some embodiments, the retail host network 110 and the client network 210 may be joined.

The client network 210 may include a client devices 216 (i.e., one or more client devices). The client device 216 may include, by way of example, a smart phone, a desktop computer, a laptop, a tablet, a phablet, a smart watch, smart glasses, wearable electronics, pager, personal digital assistant, a home assistant and/or digital concierge device, and/or another suitable electronic device, particularly a computing device configured for wireless radio frequency (RF) communication to exchange/upload/transmit/transfer information the central processing system 140, enterprise proprietary server 202, and other components of the system 100. Generally speaking, the client device 216 may be utilized to order one or more products, provide information in furtherance of retrieving one or more available coupons, and/or otherwise communicate directly and/or indirectly with components of the system 100. The client device 216 may be communicatively connected to the retail stores 112, and/or to a central processing system 140 through the digital network 130, as described below. The client device 216 may receive notifications or indications with regard to coupons coming available for a product that is often purchased by a customer, successful retrieval and application of a coupon toward a purchase, or that an order has been fulfilled and is ready for pick up. Components and features of the client device 216 will be discussed in greater detail with respect to FIG. 4.

The retail stores 112 may be located, by way of example rather than limitation, in separate geographic locations from each other, including different areas of the same city, different cities, or even different states. Each of the retail stores 112 may be, for example, an in-store retail store, an on-line store, or a mail-order store. An in-store retail store may be a "brick and mortar" store that may include one or more physical buildings or structures, where each of the retail stores 112 may accommodate shoppers and customers. As used herein, the term "retail store" refers to any of these environments (e.g., kiosks, Internet interface terminals, etc.).

The one or more retail stores 112 may include a number of workstations 128 configured to execute various product and service-related applications. The workstations 128 may be local computers located in the various retail stores 112 throughout the retail host network 110. Each workstation 128 may include a user interface application 111, a server application 113, and/or a facility server 126. Retail store personnel (not shown) may use the workstations 128 to access information relating to customers, orders, store inventory, available products, available coupons, retrieved coupons, payments, and so forth. The server application 113 may be communicatively connected with the client device 216 via the network 130. The server application 113 may be configured to receive data/files, corresponding to a client and/or an order, transmitted from the client device 216, via the network 130, and then route the received data/files to other devices (e.g., the central processing system 140, a third-party server 320, etc.).

The retail stores 112 may also include a plurality of facility servers 126 disposed instead of, or in addition to, a plurality of workstations 128. Each of the retail stores 112 may include one or more facility servers 126 that may facilitate communications between the workstations 128 of the retail stores 112 via the digital network 130, and may store information for a plurality of customers/employees/accounts/etc. associated with each facility. Unless otherwise indicated, any discussion of the workstations 128 also refers to the facility servers 126, and vice versa. Moreover, environments other than the retail stores 112 may employ the workstations 128 and the servers 126.

One or more of the front-end components 102 may be excluded from communication with the back-end components 104 by configuration or by limiting access due to security concerns. For example, the client device 216 may be excluded from direct access to the back-end components 104. In some embodiments, the retail stores 112 may communicate with the back-end components via the digital network 130. In other embodiments, the retail stores 112 and the client device 216 may communicate with the back-end components 104 via the same digital network 130, but digital access rights, IP masking, and other network configurations may deny access to the client device 216.

The back-end components 104 may include a central processing system 140, one or more enterprise proprietary servers 202, and/or one or more third-party networks 310. The central processing system 140 and the enterprise proprietary server 202 may be associated with a business enterprise or company. It should be appreciated that the term "enterprise" may be used herein with reference to such business enterprise or company that utilizes the system 100 as part of its business operations. The retail stores 112 may be communicatively connected to different back-end components 104 having one or more functions or capabilities that are similar to the central processing system 140. The central processing system 140 may include an available coupon bot 170, a coupon retrieval bot 180, a customer information database 142, an available coupon database 144, a retrieved coupon database 146, a clock component 132, and a controller 155. The controller 155 may be operatively connected to the customer information database 142 via a customer information link 152 connected to an input/output (I/O) circuit 166. The controller 155 may be operatively connected to the available coupon database 144 via an available coupon link 154 connected to the input/output (I/O) circuit 166. The controller 155 may be operatively connected to the retrieved coupon database 146 via a retrieved coupon link 156 connected to the input/output (I/O) circuit 166. In some embodiments, the customer information link 152, the available coupon link 154, and the retrieved coupon link 156 may be a single component that operatively connects the controller 155 to the customer information database 142, the available coupon database 144, and the retrieved coupon database 146 via the input/output (I/O) circuit 166. It should be noted that, while not shown, additional databases may be linked to the controller 155 in any of the aforementioned manners. The central processing system 140 may implement the server application 113 for providing data to a user interface application 111 operating on the workstations 128. The central processing system 140 may include one or more computer processors 162 adapted and configured to execute various software applications and components of the system 100, in addition to other software applications.

The controller 155 includes a program memory 160, the processor 162 (or "microcontroller" or "microprocessor"), a random-access memory (RAM) 164, and the input/output (I/O) circuit 166, all of which may be interconnected via an address/data bus 165. A link 135 may operatively connect the controller 155 to the digital network 130 through the I/O circuit 166. Although FIG. 1 depicts only one controller 155 with one microprocessor 162, one program memory 160, and one RAM 164, it should be understood that different quantities of each may be utilized or present. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example.

The program memory 160 may contain machine-readable instructions (i.e., software) 171, for execution by the processor 162. The software 171 may perform various tasks associated with the system 100 such as checking for available coupons, extracting data corresponding to available coupons, retrieving available coupons, applying retrieved coupons toward an ordered/purchased product, operating a retail store or retail stores, and/or other tasks such as those described herein. The software 171 may be a single module or may comprise a plurality of modules. The one or more computer processors 162 may execute the machine-readable instructions 171. In some embodiments, the machine-readable instructions 171 may correspond to software routines including an available coupon check routine 272, a coupon eligibility routine 274, a retrieve coupon routine 276, and/or an update retailer service routine 278.

The available coupon check routine 272 may be implemented as a series of machine-readable program instructions for causing the available coupon bot 170 to check the third-party server 320 for a registry of one or more products for which the third-party is offering a coupon. The available coupon check routine 272 may be configured to be executed by a plurality of available coupon bots 170, and/or may be executed with respect to one or more third-party servers (e.g., one third-party server 320 or more than one third-party server 320). The coupon eligibility routine 274 may be implemented as a series of machine-readable program instructions for determining whether there is a coupon available to apply toward the purchase of one or more ordered products, and if the customer is eligible (i.e., satisfies requisite criteria) to apply the one or more available coupons toward a purchase. The retrieve coupon routine 276 may be implemented as a series of machine-readable program instructions for causing the coupon retrieval bot 180 to retrieve one or more coupons, or data corresponding to one or more coupons, from a third-party (e.g., the third-party server 320). The update retailer service routine 278 may be implemented as a series of machine-readable program instructions for updating an order for one or more products as a result of obtaining and applying one or more retrieved coupons. The update retailer service routine 278 may be configured to adjust the price or transaction terms of one or more ordered/purchased products as a result of redeeming/applying one or more coupons.

The customer information database 142 stores customer data related to one or more customers of the enterprise. Customer data may include, or otherwise correspond to, one or more customers' name, phone number, e-mail address, home address, work address, date of birth, medical prescriptions, medical history, insurance information, purchase history, allergies, preferred retail pick-up location, primary physician, referring/treating physician, emergency contact information, and/or any other information related to a customer. The central processing system 140 may access data stored in the customer information database 142 when executing various functions and tasks associated with the operation of the system 100. For example, customer data stored in the customer information database 142 may be provided to a third-party serve 320, on behalf of a customer who ordered and/or purchases a qualifying product covered by an available coupon, in furtherance of retrieving the available coupon to apply toward a customer's order/purchase. Data stored in the customer information database 142 may be transmitted to the client device 216, the server application 113, facility server 126, workstation 128, etc.

The available coupon database 144 stores available coupon data corresponding to qualifying products for which one or more third-parties have made one or more coupons available for use toward the purchase of the qualifying product. The available coupon database 144 may store a list, register, table, other indication, etc. of qualifying products for which one or more coupons are available. The available coupon database 144 may store data corresponding to specific quantities, sizes, dosages, etc. of a product that qualify for use of an available coupon. For example, the available coupon database 144 may store data indicating that all body wash products 3 oz. or larger are eligible for a $1 off coupon. In some embodiments, the available coupon database 144 may store data such as a UPC or other characteristic identifier corresponding to one or more products for which a coupon is available. The available coupon database 144 may also store data relating to one or more criteria or rules which need to be satisfied in order for a coupon to be redeemable. For example, the available coupon database 144 may store data relating to a customer minimum age required to purchase a product eligible for a coupon, such as a 21-years old to purchase alcohol. The central processing system 140 may access data stored in the available coupon database 144 when executing various functions and tasks associated with the operation of the system 100.

The retrieved coupon database 146 is adapted to store retrieved coupon data corresponding to one or more coupons retrieved from a third-party (e.g., from the third-party server 320 via a third-party interface 322) for use toward the purchase of an ordered product. The retrieved coupon database 146 may store a list, register, table, grouping, other indication, etc. of one or more coupons, and/or other data corresponding to the one or more coupons. The stored coupon data may include an alphanumeric code, image, barcode, string of characters, and/or any other identifier that is extracted from a third-party and can be applied toward purchasing one or more products. The retrieved coupon database 146 may store retrieved coupon data corresponding to a specific coupon obtained for a specific customer. For example, the retrieved coupon database 146 may store data corresponding to a retrieved coupon using customer John Smith's information and to be used specifically by John Smith. Whereas in other embodiments, the retrieved coupon database 146 may store retrieved coupon data corresponding to a coupon that can be used by multiple customers and/or used multiple times. For example, the retrieved coupon database 146 may store data corresponding to a coupon code (e.g., entering the term "DOLLAROFF" at a checkout prompt) for a $1 off the purchase of a certain brand of deodorant to be used by any customer. In some embodiments, the retrieved coupon database 146 may cease storing retrieved coupon data after the associated coupon has been redeemed and/or the coupon is no longer eligible for use (e.g., the coupon expired, the products covered by the coupon have been discontinued, the products covered by the coupon are no longer offered for sale by the enterprise, etc.). The central processing system 140 may access data stored in the retrieved coupon database 146 when executing various functions and tasks associated with the operation of the system 100.

The available coupon bot 170 may be configured to extract data corresponding to one or one or more products for which a coupon can be applied toward the purchase of the one or more products. The available coupon bot 170 may extract the data from a third-party (e.g., by extracting data from the third-party interface 322 associated the third-party server 320). In some embodiments, the available coupon bot 170 may include a hardware component coupled to the central processing system 140. Whereas in some embodiments, the available coupon bot 170 may additionally or alternatively include a software application executed by various components of the central processing system 140. The available coupon bot 170 may include a plurality of subroutines. The available coupon bot 170 may include or be in communication with a data scrubbing component 172, a memory unit 174, and/or a communication unit 176. The data scrubbing component 172, or associated subroutine of the available coupon bot 170, may be configured to extract data from a third-party server, or a component thereof. In some embodiments, the data scrubbing component 172 may include an optical character recognition (OCR) component. In embodiments in which the available coupon bot 170 includes a memory unit 174, the memory unit 174 may store information extracted from the third-party interface 322, such information including, for example, a list or other indication of products for which a coupon exits (or other data corresponding thereto). The communication unit 176 may be configured to transmit the extracted data to the available coupon database 144. In some embodiments, the communication unit 176 may directly transmit the extracted data to the available coupon database 144, whereas in other embodiments the communication unit 176 may transmit the extracted data to the memory unit 174 and/or from the memory unit 174 to the available coupon database 144.

It should be appreciated that while the system 100 is depicted to include just one available coupon bot 170, the system 100 may include a plurality of available coupon bots 170 or execute a plurality of instances of available coupon bot software routines. Accordingly, a plurality of available coupon bots 170 may simultaneously retrieve a list of one or more products for which one or more coupons are available from one or more third-parties. For example, the system 100 may include three available coupon bots 170 configured to retrieve a list of products from a manufacturer that may offer three different types of products, such that three separate lists of products with an available coupon can be simultaneously extracted. Additionally, the system 100 may include one or more available coupon bots 170 dedicated to determining a list of available coupons from a specific third-party within a third-party network. For example, a first available coupon bot 170 may check a first manufacturer's website, a second available coupon bot 170 may check a second manufacturer's website, a third available coupon bot 170 may check a third manufacturer's website, etc. In such embodiments, the individual available coupon bots 170 may be specifically configured to determine the products for which the third-party is offering a coupon based on the manner/method/form in which the specific third-party server presents the list of products for which a coupon is available. For example, the data scrubbing component 172 of a first available coupon bot may be configured to extract data from a picture when the first manufacturer supplies one or more pictures of the one or more products and/or the product's packaging, whereas the data scrubbing component 172 of a second available coupon bot may be configured to extract plain text from the third-party server when the second manufacturer supplies the list of products as text on a website.

The coupon retrieval bot 180 may be configured to retrieve one or more coupons (e.g., coupons or data corresponding thereto) that are available for one or more products, from a third-party (e.g., the third-party interface 322 associated with the third-party server 320) in furtherance of applying the one or more coupons toward purchasing one or more products. In some embodiments, the coupon retrieval bot 180 may include a hardware component coupled to the central processing system 140. Additionally or alternatively, the coupon retrieval bot 180 may include a software application executed by various components of the central processing system 140. The coupon retrieval bot 180 may include a plurality of subroutines. The coupon retrieval bot 180 may include, for example, a data entry component 182, a coupon scrubbing component 184, a memory unit 186, and/or a communication unit 188. The data entry component 182, or associated subroutine of the coupon retrieval bot 180, may be configured to enter, input, or otherwise provide data to a third-party. The coupon scrubbing component 184, or associated subroutine of the coupon retrieval bot 180, may be configured to extract data from a third-party server, or a component thereof. In some embodiments, the coupon scrubbing component 184 may include an optical character recognition (OCR) component. In embodiments in which the coupon retrieval bot 180 includes a memory unit 186, the memory unit 186 may store information, or data corresponding to information, to be entered into and/or extracted from a third-party interface 322. The communication unit 188 is configured to receive data from the customer information database 142 and/or transmit extracted data to the retrieved coupon database 146. In some embodiments, the communication unit 188 may directly receive data from the customer information database 142 and/or may transmit extracted data to the retrieved coupon database 146. Whereas in other embodiments the communication unit 188 may transmit data from the memory unit 186 to third-party interface and/or transmit data from the memory unit 186 to the retrieved coupon database 146. The coupon retrieval bot 180 may be configured to operate based on checking a coupon request work queue. In such embodiments, the coupon retrieval bot 180 may process the requests in a first-in, first out manner or may process/prioritize the requests in the work queue based on any other criteria or logic (e.g., medical emergency, customer date of birth, availability of the product at the submitting or selected pick-up retail location, etc.).

In embodiments in which the coupon scrubbing component 184 includes an OCR component, an OCR standardization technique may be employed in furtherance of extracting data. For example, a window being displayed on the third-party interface 322 may need to be standardized in order to determine/calculate the location/placement for bounding boxes. The window may be standardized by checking the current width of the window, and then resizing the window to a predetermined standardized size/number of pixels (e.g., 900 pixels). Further, knowledge of a coupon size, or expected size of a coupon, may be factored into the standardization of the window and/or OCRing of a window. For example, when a window containing margins has a width of 900 pixels and the coupon is expected to have a width of 720 pixels, the width of the coupon (720 pixels) is subtract from the width of the window (900 pixels) and divided by two (for left and right margins) in order to allow the location of the bounding boxes to be properly determined in furtherance of using the OCR component.

It should be appreciated that while the system 100 is depicted to include just one coupon retrieval bot 180, the system 100 may include a plurality of coupon retrieval bots 180 or execute a plurality of instances of coupon retrieval bot software applications. Accordingly, a plurality of coupon retrieval bots 180 may simultaneously retrieve one or more coupons from one or more third-party servers, or components thereof. For example, the system 100 may have three coupon retrieval bots 180 configured to retrieve coupons from a manufacturer, such that three separate requests to retrieve a coupon can be simultaneously processed. Additionally, the system 100 may include one or more coupon retrieval bots 180 dedicated to retrieving coupons from a specific third-party server within the third-party network 310. For example, a first coupon retrieval bot 180 may only retrieve coupons from a first manufacturer, a second coupon retrieval bot 180 may only retrieve coupons from a second manufacturer, a third coupon retrieval bot 180 may only retrieve coupons from a third manufacturer, etc. In such embodiments, the individual coupon retrieval bots 180 may each be specifically configured to retrieve a coupon based on the manner/method/form in which the specific third-party server delivers the coupon. For example, the coupon scrubbing component 184 of a first coupon retrieval bot 180 may be configured to extract data from a bar code when the first manufacturer supplies a coupon as a bar code, whereas the coupon scrubbing component 184 of a second coupon retrieval bot 180 may be configured to extract plain text from a coupon when the second manufacturer supplies a coupon as an alphanumeric scheme. In another example, the system 100 may have three coupon retrieval bots 180 configured to each retrieve a separate coupon for the same product from three different third-parties such that three different coupons can be applied toward the purchase of one product.

It should be appreciated that in some embodiments, some components described and depicted as separate components may be a single component. For example, in some embodiments, the communication unit 174 and the communication unit 188 may be the same component(s).

The clock component 132 may be configured to manage time or frequency based execution of one or more components of the central processing system 140. In some embodiments, the clock component 132 is configured to manage/dictate/define the intervals at which the available coupon bot 170 checks the one or more third-party servers, or component thereof, for the one or more products for which the third-party is offering a coupon. In some embodiments, the clock component 132 is configured to manage/dictate the intervals at which the coupon retrieval bot 180 checks to see if a coupon is available to be printed, downloaded, viewed, saved, opened, have its information extracted, or otherwise handled in furtherance of obtaining information related to retrieving the coupon. In some embodiments, the clock component 132 may be an analog or digital up-counter or down-counter.

It should be appreciated that the systems and methods described herein and/or any embodiments thereof may comprise different quantities and/or types of the components described. For example, although FIG. 1 depicts the system 100 as including one central processing system 140 in communication with three retail stores 112, one client device 216, etc., it should be understood that different numbers of processing systems, retail stores, third-party servers, devices, and described components thereof may be utilized. For example, the digital network 130 (or other digital networks, not shown) may interconnect the central processing system 140 to a plurality of proprietary servers 202, hundreds of retail stores 112, multiple third-party servers 320, and thousands of client devices 216. Similarly, in some embodiments, multiple components may be just a single component. For example, in some embodiments, the customer information database 142, the available coupon database 144, and the retrieved coupon database 146 may be a single database.

The third-party network 310 may comprise one or more third-party servers 320 associated with a third-party merchant, manufacturer, or other provider of goods and/or services. It should be appreciated that in some embodiments, the third-party network 310 may be any third-party that possesses information relating to products for which a coupon is available and/or that can otherwise issue/provide such coupons. For example, in some embodiments, the third-party may be a website that provides advertisements for a retailer or manufacturer of goods and services. Keeping with such an example, the third-party may be website for a golf magazine that is offering a coupon for a free-trial of a specific prescription medication. A third-party server 320 may include various hardware and software for implementing a third-party interface 322, through which information relating to a product may be exchanged. In one embodiment, for example, the third-party server 320 may be a server associated with a manufacturer of a prescription drug and the third-party interface 322 may be a dedicated webpage or application through which information is exchanged relating to the one or more prescription drugs manufactured and/or sold by the manufacturer. In such example, the dedicated webpage may provide information relating to one or more of the manufacturer's prescription drugs which are eligible for a coupon, rebate, free trial, etc., and/or may collect customer information in furtherance of issuing such coupon, rebate, free trial, etc. The third-party server 320 may include similar components and/or functionality as the central processing system 140 and the enterprise proprietary server 202.

Figure 2:
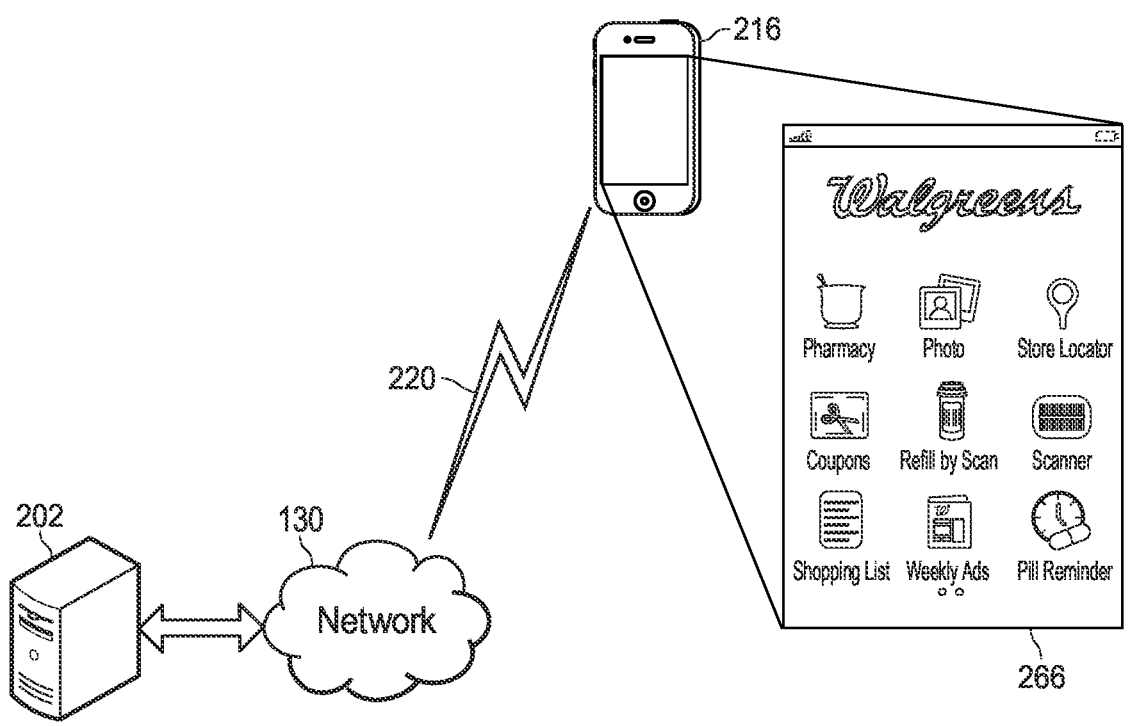
FIG. 2 illustrates a block diagram of the system of FIG. 1, in accordance with some embodiments.

FIG. 2 illustrates a block diagram of an embodiment of the system 100 in which an enterprise proprietary server 202 and the client device 216 are connected via the network 130. In some embodiments of implementing the system 100, a user may initiate and interact with the enterprise proprietary server 202 and the retail store systems via a client device 216, a specialized application such as the client application 266, or a plurality of web pages. In some instances, the client device 216 may communicate with the network 130 via wireless signals 220 and, in some instances, may communicate with the network 130 via an intervening wireless or wired device (not shown), such as a wireless router, wireless repeater, base transceiver station of a mobile telephony provider, etc. The client device 216 may interact with the enterprise proprietary server 202 to receive web pages or server data from the enterprise proprietary server 202 and may display the web pages or server data via a client application 266. It should be appreciated that although only one enterprise proprietary server 202 is depicted in FIG. 2, multiple enterprise proprietary servers 202 may be provided for the purpose of distributing server load, serving different web pages, implementing different portions of the retail store web interface, etc. These multiple enterprise proprietary servers 202 may include a web server, an entity-specific server (e.g., an Apple® server, etc.), a server that is disposed in a retail or proprietary network, etc.

II. Example Server and Client Devices

Figure 3:
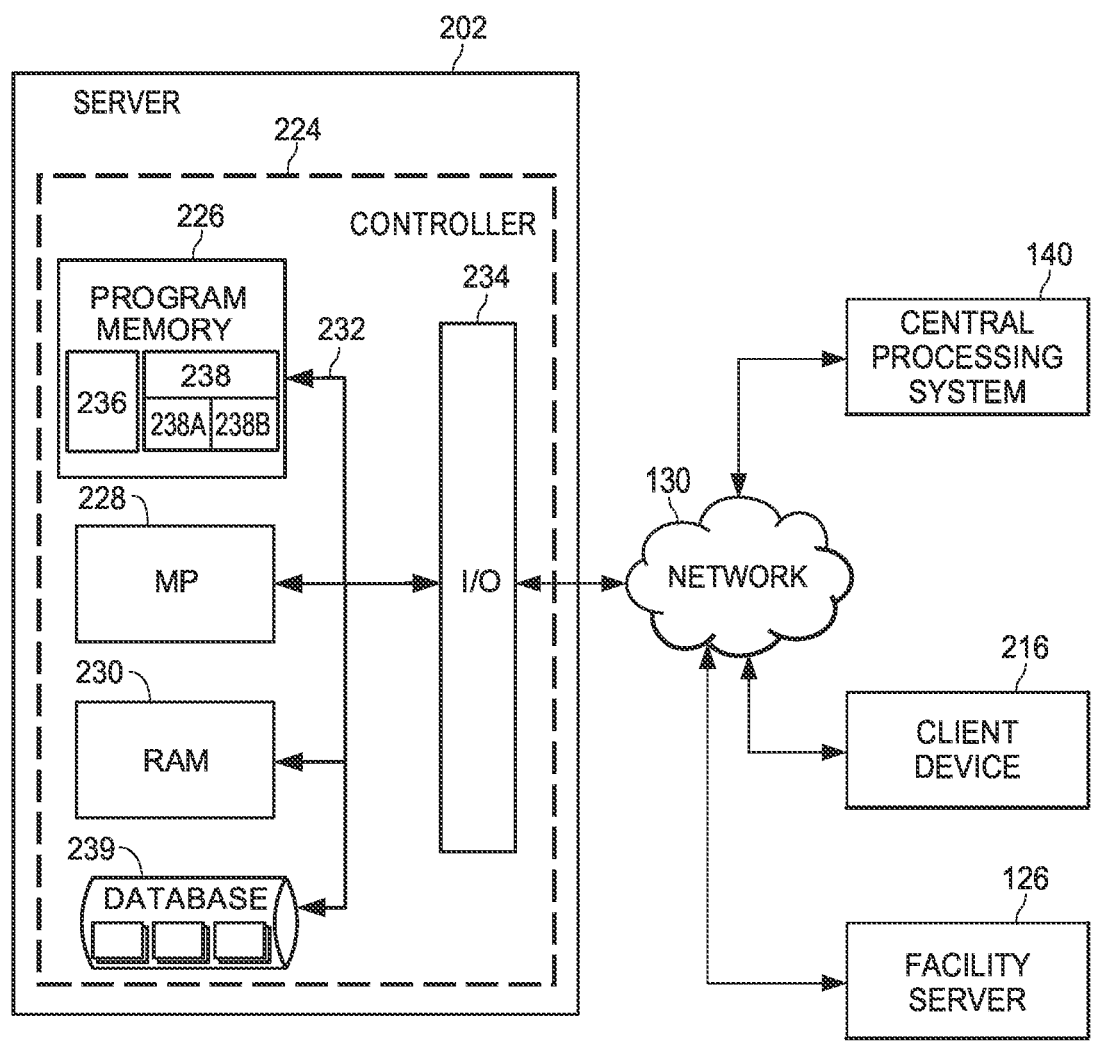
FIG. 3 illustrates a block diagram of an enterprise proprietary serve, in accordance with some embodiments.

FIG. 3 illustrates an embodiment of the enterprise proprietary server 202. The enterprise proprietary server connects to the central processing system 140, the facility server 126, and/or the client device 216 via the network 130. The enterprise proprietary server 202 includes a controller 224. The controller 224 includes a program memory 226, a microcontroller or a microprocessor (MP) 228, a random-access memory (RAM) 230, and an input/output (I/O) circuit 234, all of which are interconnected via an address/data bus 232. The controller 224 may implement the RAM(s) 230 and the program memories 226 as semiconductor memories, magnetically readable memories, and/or optically readable memories, for example. In some embodiments, the controller 224 may also include, or otherwise be communicatively connected to, a database 239 or other data storage mechanism (e.g., one or more hard disk drives, optical storage drives, solid state storage devices, etc.). The database 239 may store data such as customer web profiles, product data, mobile device application data, web page templates and/or web pages, and other data used to interact with the customer via the client device 216 and through the network 130.

In some embodiments, the enterprise proprietary server 202 may act as a routing or interfacing server between the client device 216, and the central processing system 140 in order to assist in facilitating some of the functionality of the system 100. For example, the enterprise proprietary server 202 may be configured to communicate with the central processing system 140, and/or the client device 216 via a multitude of protocols, such as packet-switched protocols, web services, web APIs (Application Programming Interface), etc. The enterprise proprietary server 202 may also convert (if necessary) and route client application data (not shown) to the appropriate server, such as the central processing system 140. In some embodiments, the enterprise proprietary server 202 may act as the destination server and need not route any data from the client device 216. It should be appreciated that references made throughout this disclosure to transmitting/receiving orders/coupons/data/files/etc. to and/or from the central processing system 140 may also include transmitting/receiving orders/coupons/data/files/etc. to and/or from the enterprise proprietary server 202, either directly or indirectly.

The program memory 226 and/or the RAM 230 may store various applications for execution by the microprocessor 228. For example, a user-interface application 236 may provide a user interface to the enterprise proprietary server 202, which may, for example, allow a network administrator to configure, troubleshoot, or test various aspects of the server's operation, or otherwise to access information thereon. A server application 238 may operate to populate and transmit client application data and web pages to the client device 216, receive information from the client device 216 transmitted back to the enterprise proprietary server 202, and/or forward appropriate data to the central processing system 140, and the facility servers 126. The server application 238 may be a single module 238 or a plurality of modules 238A, 238B. While the server application 238 is depicted in FIG. 3 as including two modules, 238A and 238B, the server application 238 may include any number of modules accomplishing tasks related to implantation of the enterprise proprietary server 202. By way of example, the module 238A may populate and transmit the client application data and/or may receive and evaluate inputs from the user to receive a data access request, while the module 238B may communicate with one or more of the back end components 104 to fulfill a data access request. Although FIG. 3 depicts only one controller with one microprocessor 228, one program memory 228, and one RAM 230, it should be understood that different quantities of each may be utilized or present. Similarly FIG. 3 depicts the I/O circuit 234 as a single block, the I/O circuit 234 may include a number of different types of I/O circuits.

Figure 4:
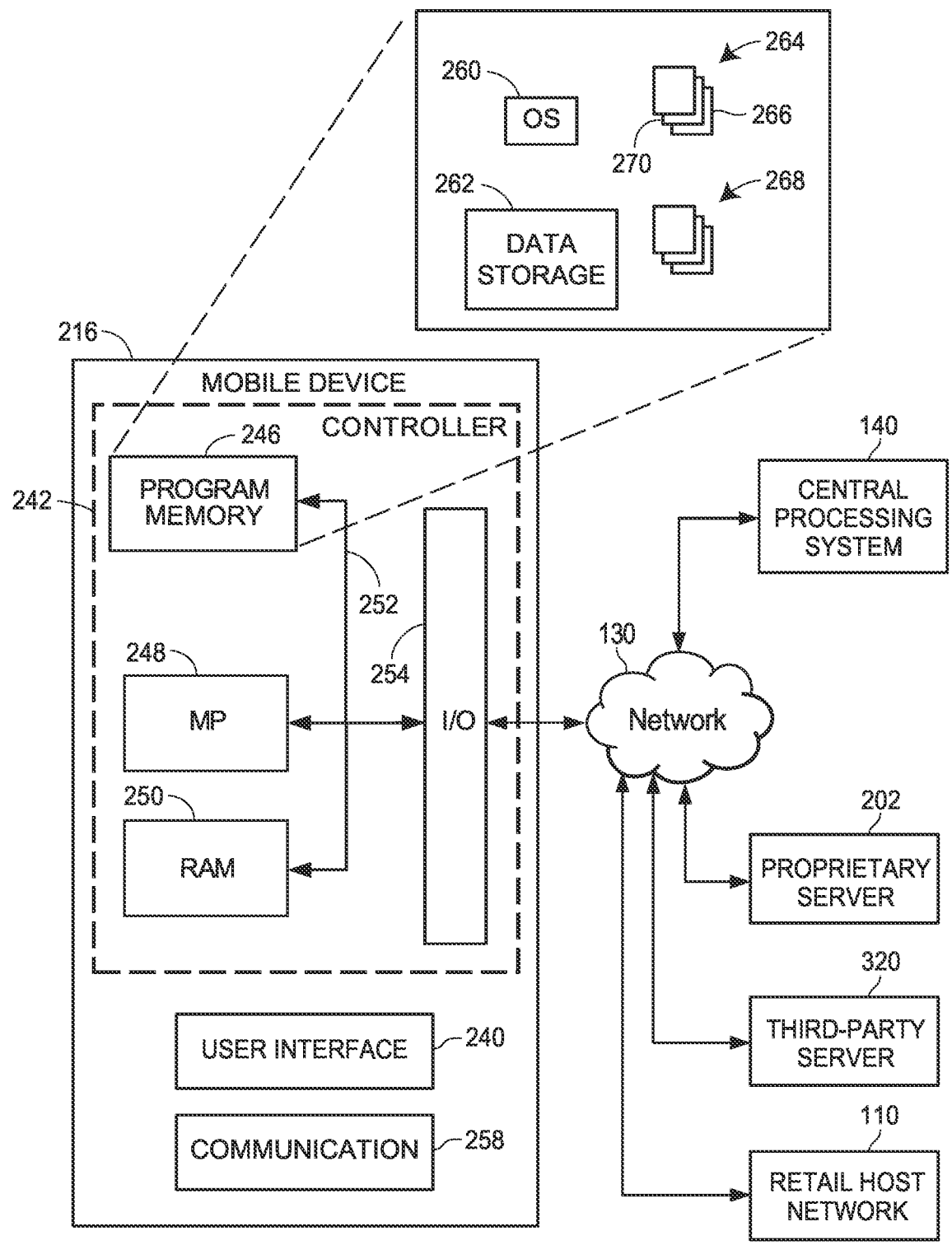
FIG. 4 illustrates a block diagram of a client device, in accordance with some embodiments.

FIG. 4 illustrates a block diagram of an embodiment of the client device 216. The client device 216, or a plurality of client devices, may be configured to communicate with the central processing system 140, enterprise proprietary server 202, third-party server 320, and/or other components of the retail host network 110 in connection with ordering/purchasing one or more products, agreeing to terms and conditions for obtaining one or more coupons, submitting a form to obtain one or more coupons, and/or any other functionalities described herein. The client device 216 may connect via the network 130 to the central processing system 140, enterprise proprietary server 202, third-party server 320, and/or other components of the retail host network 110. The client device 216 may include a user interface 240, a controller 242, and/or a communication unit 258.

The user interface 240 may be configured to present information to the user and/or receive inputs from the user, and may accordingly include a set of I/O components (e.g., capacitive or resistive touch sensitive input panels, keys, buttons, lights, LEDs, cursor control devices, haptic devices, and others). In some embodiments, the user interface 240 may include a touchscreen display using singular or combinations of display technologies and can include a thin, transparent touch sensor component superimposed upon a display section that is viewable by a user. For example, such displays may include capacitive displays, resistive displays, surface acoustic wave (SAW) displays, optical imaging displays, and the like. The user interface 240 may include one or more user-input devices (not shown). In some embodiments, the user-input device may include a "soft" keyboard that is displayed on a display/screen of the client device 216, an external hardware keyboard communicating via a wired or a wireless connection (e.g., a Bluetooth keyboard), an external mouse, and/or any other suitable user-input device(s). In some embodiments, the user input device may include one or more auxiliary input ports such as a USB, lightning port, audio out, video out, etc. The user interface 240 may also include one or more user output devices (not shown) configured to connect the client device 216 to additional components. For example, the user output device may include one or more auxiliary output ports such as a USB, lightning port, audio out, video out, etc. The user output device may be configured to connect to a television, computer, phone, virtual reality hardware, monitor, or other electronic device. It should be appreciated that in some embodiments, the user input device and user output device may be a single I/O component.

The controller 242 may include a program memory 246, one or more microcontroller or a microprocessor (MP) 248, a random-access memory (RAM) 250, and/or an input/output (I/O) circuit 254, all of which may be interconnected via an address/data bus 252. The program memory 246 may include an operating system 260, a data storage 262, a plurality of software applications 264, and/or a plurality of software routines 268. The operating system 260, for example, may include one of a plurality of mobile platforms such as the iOS®, Android™ Palm® webOS, Windows Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 262 may store data such as media content, user profiles, application data for the plurality of applications 264, routine data for the plurality of routines 268, and/or other data used to interact with the enterprise proprietary server 202, the central processing system 140, the facility servers 126, the third-party server 320, and/or the server applications 113 through the digital network 130. In some embodiments, the controller 242 may also include, or otherwise be communicatively connected to, other data storage mechanisms (e.g., one or more hard disk drives, optical storage drives, solid state storage devices, etc.) that may reside within the client device 216. Although FIG. 4 depicts only one controller 242 with one microprocessor 248, one program memory 246, and one RAM 250, it should be understood that different quantities of each may be utilized or present. Similarly FIG. 4 depicts the I/O circuit 254 as a single block, the I/O circuit 254 may include a number of different types of I/O circuits. The controller 242 may implement the RAM(s) 250 and the program memories 246 as semiconductor memories, magnetically readable memories, and/or optically readable memories, for example. The communication unit 258 may communicate with the enterprise proprietary server 202 via any suitable wireless communication protocol network (e.g., GSM, CDMA, TDMA, WCDMA, LTE, EDGE, OFDM, GPRS, EV-DO, UWB, IEEE 802 including Ethernet, WiMAX, Wi-Fi, Bluetooth, and others). In some embodiments, the communication unit 258 includes a transceiver.

The one or more processors 248 may be adapted and configured to execute any one or more of the plurality of software applications 264, any one or more of the plurality of software routines 268 residing in the program memory 242, and/or other software applications/routines. One of the plurality of applications 264 may be a client application 266 that may be implemented as a series of machine-readable instructions for performing the various tasks associated with receiving information at, displaying information on, and transmitting information from the client device 216. One of the plurality of applications 264 may be a native web browser 270, such as, for example, Apple's Safari®, Google Android™ mobile web browser, Microsoft Internet Explorer® for Mobile, Opera Mobile™, that may be implemented as a series of machine-readable instructions for receiving, interpreting, and displaying web page information from the enterprise proprietary server 202, the facility servers 126, or the server applications 113 while also receiving inputs from the user. In such embodiments, the native web browser 270 may be presented via the user interface 240 to enable a user to enter, select, confirm, and/or submit data.

For example, the client device 216 may include a database of files 239 within the memory. In some embodiments, the database 239 may be additionally or alternatively stored at a server (e.g., facility server 126, etc.) and/or another third party server (such as one associated with DropBox, Amazon, Google Drive, iCloud, etc.). In some embodiments the database 146 may store at least some of the same data as the database 239. Although FIG. 4 depicts the database 239 as coupled to the client device 216, it is envisioned that the database 239 may be maintained in the "cloud" such that any element of the environment 100 capable of communicating over the network 130 may directly interact with the database 239.

Generally, the term "user" is used when referring to a person who is operating one of the client device 216 and is not exclusive of the term "customer." Further, it should be appreciated that the term user may refer to two or more individuals.

As shown in FIG. 2, the user may execute the client application 266 on the client device 216 to access the enterprise proprietary server 202, the facility servers 126, and/or the server applications 113. Using the client application 266, the user may request server data (not shown) by navigating a series of client application screens, such as a home screen of the client application 266. The user may launch the client application 266 from the client device 216 via any suitable manner, such as touch-selecting a client application icon (not shown) on the display 240 of the client device 216, double-clicking on the client application icon via a mouse of a computer or a trackpad of a laptop.

In operation of an embodiment of the system 100, the central processing system 140 may execute program instructions to cause the available coupon bot 170 to extract information from the third-party server 320 to identity of one or more products for which a coupon is available to apply toward purchasing the one or more products. After extracting information corresponding to the identity of the one or more products for which a coupon is available, the available coupon bot 170 may transmit the extracted information to the central processing system 140, and the extracted information may be stored in the available coupon database 144. This processes may continue throughout a predetermined interval (e.g., every two minutes) or for a frequency that as managed by the clock component 132 such that the available coupon database 144 is always up to date with valid, available coupons. When a request to order one or more products is submitted to the central processing system 140, the central processing system 140 may execute program instructions to determine whether the one or more ordered products qualify or otherwise are eligible to have a coupon applied based on the information of available coupons stored in the available coupon database 144 and/or customer information submitted with the order and/or stored in the customer information database 142. To determine if a coupon is eligible to be applied, the central processing system 140 may cross-reference information corresponding to the order with data stored in the available coupon database 144. If the central processing system 140 determines that there is one or more coupons available to apply toward the one or more ordered products, the central processing system 140 may execute program instructions to cause the coupon retrieval bot 180 to obtain the one or more available coupons, or information corresponding to the one or more available coupons, from the third-party server 320 offering the coupon. After retrieving the coupon, or information corresponding to the coupon, the coupon retrieval bot 180 may transmit the retrieved coupon to the central processing system 140 and the retrieved coupon is stored in the retrieved coupon database 146. The retrieved coupon may be redeemed/applied toward the purchase for the one or more products.

III. Example Signal Diagram

Figure 5:
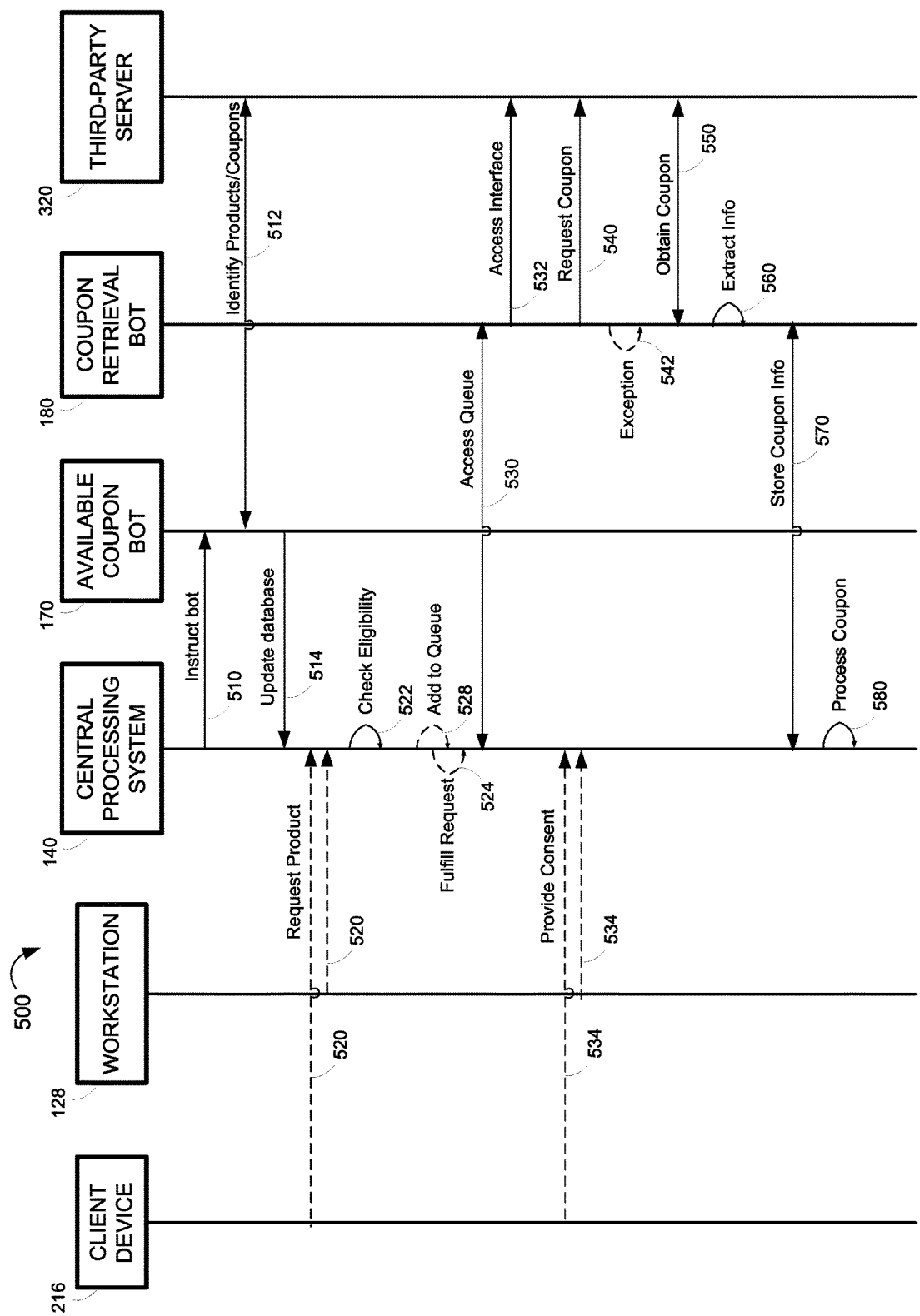
FIG. 5 illustrates a signal diagram associated with managing coupons, in accordance with some embodiments.

FIG. 5 illustrates an example signal diagram 500 associated with automatically determining available coupons and retrieving an available coupon to apply toward purchasing a product. The signal diagram 500 may begin when one or more computer processors 162 of the central processing system 140 executes (510) program instructions to cause the available coupon bot 170 to connect to and analyze a third-party interface 322 associated with a third-party server 320 (e.g., via a third-party interface 322) in furtherance of determining one or more products for which a coupon is available/offered by the third-party. In some embodiments, the available coupon bot 170 may interact with the third-party server 320 by opening an internet application and connecting to the website of a product manufacturer. The available coupon bot 170 may traverse the third-party interface 322 in order to reach a webpage providing a listing, or other indication, of one or more products for which a coupon is available.

During execution of these program instructions, the available coupon bot 170 extracts/scrubs the third-party interface 322 (512) to identity of the one or more products for which a coupon is available. These program instructions may be executed with a specified time frequency (e.g., once every minute, hour, day, etc.), based on a specified event (e.g., a predetermined number of orders/sales by an enterprise), based on a manual request, and/or based on other logic (e.g., exceeding a threshold of available space in database) in order to enable the available coupon bot 170 to continuously or routinely search for available coupons and keep the available coupon database 144 up-to-date.

After extracting the list of one or more products for which a coupon is available, the bot may store/update data (514) corresponding to the one or more of products in the available coupon database 144. In some embodiments, the bot may compare the existing data stored in the available coupon database 144 with the data extracted from the third-party interface 322 to prevent storing of duplicate information (i.e., making multiple entries of the same available coupon for a single product). However, it should be appreciated that the multiple coupons from the same or difference third-party servers may apply to a single product, and in such situations data corresponding to the multiple coupons may be stored in the available coupon database 144. It should also be appreciated, that in some embodiments the bot may compare the extracted list of products with data corresponding to products offered for sale by the enterprise, and then only save data corresponding to the extracted list of one or more products in the available coupon database 144 for the products which the enterprise offers for sale. In such embodiments, the bot may store data corresponding to the extracted list of one or more products that the enterprise does not offer for sale in a different data storage unit to be available for other purposes (e.g., determining products to potentially sell, determining alternatives to products currently offered for sale, etc.). It should also be appreciated that in some embodiments, the available coupon bot 170 may cause a coupon retrieval bot 180 to automatically retrieve and store the one or more available coupons.

The central processing system 140 may receive a command/request (520) to order, purchase, or otherwise supply one or more products. In some embodiments, such command/request (520) may be initiated at a workstation 128 associated with a retail location 111 (e.g., by an employee of the enterprise, such as a pharmacist, submitting a prescription), a client device 216 (e.g., a customer submitting a prescription using the enterprise application 266 and/or the client device 216), or by another third-party (e.g., a physician submitting a prescription on behalf of a patient). Data corresponding to the request to order and/or purchase the product may be stored in a database such as the customer information database 142.

After receiving the request to order and/or purchase the product (e.g., in response thereto), the central processing system 140 may execute program instructions to check the eligibility (522) of the one or more products for an available coupon. The central processing system 140 may analyze data corresponding to the one or more products and data stored in the available coupon database 144. For example, the central processing system 140 may compare the name, type, ingredients, manufacturer, and/or other characteristics of the one or more products with the same or similar parameters as those stored in the available coupon database 144. In some embodiments, the central processing system 140 may conduct additional analysis/determinations, based on data associated with the request to order/purchase the products, in furtherance of determining the availability, usability, or eligibility of the one or more available coupons. The central processing system 140 may ensure, based on analyzing data stored in the customer information database 142, that the customer (for whom the product has been ordered) satisfies one or more criteria/qualifications and/or rules associated with the available coupon and/or product. For example, the central processing system may ensure that the customer is old enough to purchase the product, has not previously used the available coupon toward purchasing the product, the product is covered by the customer's insurance, the customer has not already exceeded a maximum purchase/disbursement quantity, the customer does not have an allergy to the product, the customer is legally allowed to own the product, etc.

If there are one or more coupons available for the one or more products, and the customer is eligible for the one or more coupons, the central processing system 140 may add a request to attain the available coupon for the one or more products to a coupon request work queue (528). In contrast, if there are no coupons available for the one or more products, or there were one or more available coupons but the customer was not eligible to use the one or more available coupons, the central processing system 140 may proceed to fulfill (524) the request to order/purchase the one or more products (i.e., without coupons).

A coupon retrieval bot 180 may be configured to check the coupon request work queue for requests to obtain an available coupon (530). The coupon retrieval bot 180 may process the requests in a first-in, first out manner or may process/prioritize the requests in the work queue based on any other criteria or logic (e.g., medical emergency, customer date of birth, availability of the product at the submitting or selected pick-up retail location, etc.). For example, a first request to order the product may be submitted by a first customer in Chicago at 10:00 PM CST, who intends to pick up the ordered product from a retail location that is already closed for the day, while a second request to order the product is submitted by a second customer in Los Angeles at 11:00 PM CST, who intends to pick up the ordered product from a retail location open 24-hours. In such example, the coupon retrieval bot 180 may process the second customer's request for the available coupon prior to processing the first customer's request for the available coupon because the second customer's order is capable of being fulfilled prior to the first customer's order. In processing a request for the available coupon, the coupon retrieval bot 180 may connect to the third-party server 320 (532) to access the third-party server interface 322. In some embodiments, this may include the coupon retrieval bot 180 opening an internet application and connecting to the website of the manufacturer of the product offering the coupon. In some embodiments, the coupon retrieval bot 180 may be configured to traverse the third-party interface 322 in order to reach a coupon request form to obtain the coupon.

In some embodiments, the coupon retrieval bot 180 may populate information query fields of the coupon request form based on customer information contained in the request to order the one or more products and/or customer information stored in the customer information database 142. Once the coupon retrieval bot 180 has completed entering the requisite information into the coupon request form, the coupon retrieval bot 180 may submit the form. It should be appreciated that in some embodiments, based on regulatory and/or jurisdictional (i.e., city, county, state, country, federal, etc.) laws, the customer may need to agree to the terms and conditions or provide consent (534) for the coupon retrieval bot 180 to provide information and/or submit the coupon request form on behalf of the customer. Additionally, in some embodiments, based on regulatory and/or jurisdictional laws, the coupon retrieval bot 180 may fill out the coupon request form but the customer may be required to manually agree to the terms and conditions of the coupon and/or manually submit/approve the coupon request form. In such embodiments, the coupon retrieval bot 180 may cause the central processing system 140 to initiate a communication to the customer such that the customer can agree to the terms and conditions and/or approve or otherwise submit the coupon request form. In these embodiments, the central processing system 140 may, for example (1) initiate a telephone call in which the customer provides verbal or key-entered commands, (2) transmit a notification via the enterprise application 266 for the customer to approve/submit the form, may transmit a deep link (via the enterprise application 266, text message, e-mail, etc.) containing a URL or other pointer that, when invoked, directs the customer to the third-party interface 322 to approve/submit the form, and/or (3) transmit/receive any other type of communication that enables the customer to comply with jurisdictional requirements/laws for agreeing to terms and conditions and/or submitting information and/or obtaining the coupon.

It should be appreciated that in some embodiments, the (534) may not exist or be necessary depending on how the coupon is made available. For example, in embodiments in which the available coupon is automatically presented on the third-party interface 322, the automatic coupon bot 180 may not undertake (534) and may instead skip to (540).

After the coupon request form has been submitted (540), the coupon retrieval bot 180 may check to see if the coupon has been presented via the third-party interface 322, downloaded, or otherwise generated. In some embodiments, the coupon retrieval bot 180 may be configured to check for the coupon based on a predetermined frequency (e.g., every 10 seconds, every minute, etc.). Whereas in other embodiments, to avoid situations in which the coupon retrieval bot 180 may get stuck in an endless loop because an error has occurred, and thus the coupon may never be available, the coupon retrieval bot 180 may be configured to make a predetermined number of checks for the coupon (e.g., cycle through three iterations of checking every 60 seconds, check as many times as possible within 60 seconds, etc.). In such embodiments, the coupon retrieval bot 180 may throw an exception (542), which may trigger execution of other program instructions for the coupon retrieval bot 180 to transmit and store information about the exception on the central processing system 140 such that the exception may be analyzed.

Once the coupon has been presented via the third-party interface 322, downloaded, or otherwise generated by the third-party server 320, the coupon retrieval bot 180 may transmit a request (550) to print, download, save, open a new window, or otherwise handle the generated coupon. In some embodiments, the coupon retrieval bot 180 may again check to see if the request has been completed, in a similar manner as described with respect to (540). It should be appreciated that in some embodiments (540) and (550) may be a joint operation, whereas in other embodiments they may be separate. For example, (550) may be needed in embodiments in which the coupon is automatically presented on a webpage after submitting the coupon request form. Whereas in other embodiments, for example, the third-party server 320 may automatically generate a downloadable PDF file containing the coupon in response to submission of the coupon request form. In some embodiments, the coupon retrieval bot 180 may transmit the generated coupon directly to the customer via e-mail, text message, enterprise application 266 correspondence, and/or may save a copy of the coupon such that the customer has a record of the coupon and has been given proper notice of the terms and/or conditions of the coupon.

The coupon retrieval bot 180 may extract/read/scrub values (560) from the generated coupon. In some embodiments, the coupon retrieval bot 180 may use an optical character recognition (OCR) component to obtain the relevant coupon information from the generated coupon. In some embodiments, the coupon retrieval bot 180 may modify the third-party interface 322, the window of the downloaded coupon, or whatever other medium in which the generated coupon has been presented in order to standardize or conform to a specific characteristic (size, pixel, etc.) for the OCR component. Accordingly, such novel standardizing/resizing/modification techniques enable the OCR component to calculate the location of the bounding boxes for the information/values (e.g., PCN, BIN, and/or GRP) that need to be obtained in order to successfully apply the coupon toward the purchase of the underlying product.

Data containing/corresponding to the extracted coupon information is stored in the retrieved coupon database 146 (570). After the extracted coupon information is stored in the retrieved coupon database 146, the central processing system 140 may execute the update retailer service routine 278. The coupon may be processed (580), along with data stored in the customer information database 142, in furtherance of fulfilling the request to order and/or purchase the one or more products. In some embodiments, the central processing system 140 may transmit a notification to the client device 216, to the one or more retail stores 112, and/or to the one or more workstations 128, the notification indicating that the one or more coupons were successfully applied to the user's order/purchase or otherwise redeemed. Such notification may include a text message, e-mail, telephone call, push notification, enterprise application 266 notification, fax, and/or other correspondence.

IV. Example Computer-Implemented Method

Figure 6:
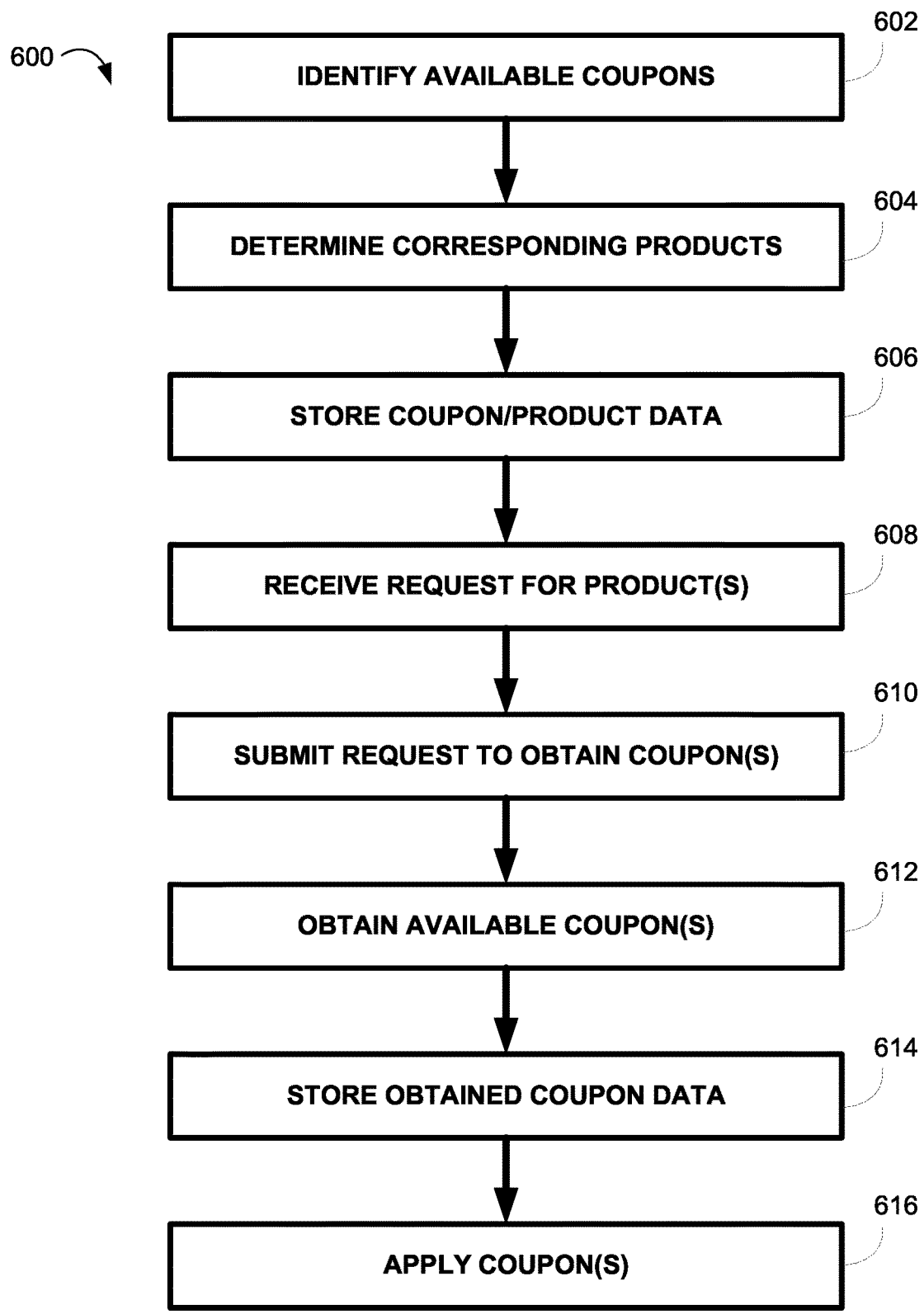
FIG. 6 illustrates an exemplary computer-implemented method of managing coupons, in accordance with some embodiments.

FIG. 6 illustrates an exemplary computer-implemented method 600 for managing coupons. The method 600 may be implemented as described above with FIGS. 1-5. In particular, the method 600 may include any of the actions of the signal diagram 500 as depicted in FIG. 5. Actions described herein may be performed in any suitable order or combination, and via various suitable computing arrangements. Where computing components are mentioned herein, the computing components may refer to corresponding computing components as described with respect to FIGS. 1-5. In some embodiments, one or more computer memories may store non-transitory computer-executable instructions that, when executed via one or more processors, cause a computing system to perform actions of the method 600. In some embodiments, the non-transitory computer-executable instructions may be stored via one or non-transitory computer-readable media.

The method 600 may include accessing a third-party server to identify one or more available coupons (602). For example, program instructions corresponding to a coupon check routine (e.g., the coupon check routine 272) may be executed by a central processing system (e.g., the central processing system 140 of FIG. 1) to cause an available coupon bot (e.g., the available coupon bot 170 of FIG. 1) to analyze the third-party server (e.g., the third-party server 320 of FIG. 1) for a list of one or more products for which a coupon is available to be applied toward the purchase of the one or more products. In some embodiments, a clock component (e.g., clock component 132 of FIG. 1) may define a frequency with which the central processing system causes the available coupon bot to analyze the third-party server.

The method 600 may include determining one or more corresponding products for which the one or more available coupons may be applied toward purchasing the one or more corresponding products (604). For example, the central processing system may cause the available coupon bot to identify, for each of the one or more identified coupons, one or more corresponding products to which the coupon may be applied.

The method 600 may include storing data corresponding to the one or more products for which the one or more coupons are available, such that the one or more available coupons may be applied toward one or more purchases of the one or more products (606). For example, the available coupon bot may provide data corresponding to available coupons and corresponding products to the central processing system, and the coupon/product data may be stored at an available coupon data base at the central processing system.

The method 600 may include receiving a request to purchase the one or more products (608). That is, one or more products for which the request is received may at least partially correspond to the stored product data (i.e., products for which coupons are available). In some embodiments, the request for the one or more products may be received at the central processing system, from either or both of a client device (e.g., client device 216 of FIG. 1) or workstation (e.g., workstation 128 of FIG. 1). In some embodiments, the method 600 may include, subsequent to receiving the request, analyzing the request to determine whether the one or more requested products qualify for the one or more coupons in the case of that particular request. In some embodiments, the central processing system may execute a coupon eligibility routine (e.g., the coupon eligibility routine 274 of FIG. 1) to analyze the request. Determining whether the one or more products qualify for the one or more coupons may include analyzing the request with respect to one or more criteria, for example one or more criteria corresponding to a customer from whom the request was received. If coupons do not apply, the request may be fulfilled without coupons, in some embodiments. If coupons do apply, the request may be added to a work queue at the central processing system, in some embodiments.

The method 600 may include, in response to the request to purchase the one or more products (and/or based on eligibility/qualification), submitting a request to obtain the one or more available coupons from the third-party server (610). In some embodiments, the central processing system may execute a retrieve coupon routine (e.g., the retrieve coupon routine 276) to invoke a coupon retrieval bot (e.g., the coupon retrieval bot 180 of FIG. 1) to access a work queue and/or retrieve the one or more available coupons. In some embodiments, the available coupon bot may automatically fill out a coupon request form by automatically completing one or more fields based on available coupon information such that the coupon may be obtained. In some embodiments, the coupon request form may require approval by the customer (e.g., via client device 216 or workstation 128 upon reviewing the coupon request form).

The method 600 may include obtaining the one or more available coupons from the third-party server (612). In some embodiments, invoking the retrieve coupon routine may cause the coupon retrieval bot to obtain the one or more available coupons. The coupon retrieval bot may, for example, obtain a PDF or webpage comprising information corresponding to the coupon. In some embodiments, further processing may be needed to obtain the information content of the coupon. Accordingly, the coupon retrieval bot may, for example, (1) determine a format of the one or more obtained coupons (e.g., a layout of the PDF/webpage indicating location of PCN, BIN, GRP, and/or other values), (2) standardize the one or more obtained coupons based on the determined format (e.g., standardizing the PDF/webpage layout), and/or (3) extract coupon data from the one or more obtained coupons (e.g., via an OCR component).

The method 600 may include storing coupon data corresponding to the one or more obtained coupons (614). Obtained coupon data may be stored, for example, at a retrieved coupon database (e.g., retrieved coupon database 146) at the central processing system. The stored coupon data may include, for example, values extracted via the formatting/OCR techniques described above.

The method 600 may include applying the one or more obtained coupons toward the requested purchase of the one or more products (616, e.g., based on the obtained/stored coupon data). In some embodiments, at some point after obtaining the coupon data, storing the coupon data, and/or applying the coupon, the central processing system may provide a notification to the customer (e.g., at the client device 216 or workstation 128) to inform the customer of the status of coupons to the request. In some embodiments, the method 600 may further include executing the purchase with the one or more coupons applied.

V. Machine Learning Techniques

In some embodiments, available coupons may be determined and/or retrieved using machine learning techniques, such as cognitive learning, deep learning, combined learning, heuristic engines and algorithms, and/or pattern recognition techniques. For example, the enterprise proprietary server, the available coupon bot, the coupon retrieval bot, the client application, a processor, etc. may be trained using supervised or unsupervised machine learning, and the machine learning program may employ a neural network, which may be a convolutional neural network, a deep learning neural network, or a combined learning module or program that learns in two or more fields or areas of interest. Machine learning may involve identifying and recognizing patterns in existing data in order to facilitate making predictions for subsequent data. For example, the frequency with which the available coupon bot checks one or more third-party servers may be influenced based on analyzed data indicating that new coupons are uploaded every Tuesday at 9:00 AM CST. Models may be created based on example inputs in order to make valid and reliable predictions for novel inputs.

Additionally or alternatively, the machine learning programs may be trained by inputting sample data sets or certain data into the programs, such as image, video, audio, mobile device, retailer database, customer information, product, and/or third-party database data. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or machine learning.

In supervised machine learning, a processing element may be provided with example inputs and their associated outputs, and may seek to discover a general rule that maps inputs to outputs, such that when subsequent novel inputs are provided the processing element may, based on the discovered rule, accurately predict the correct output. In unsupervised machine learning, the processing element may be required to find its own structure in unlabeled example inputs. In one embodiment, machine learning techniques may be used to extract the relevant data for one or more coupons, one or more products, customer orders, user device sensors, geolocation information, customer information, the retailer database, a third-party database, and/or other data.

In one embodiment, a processor (and/or machine learning or heuristic engine or algorithm discussed herein) may be trained by providing it with a large sample of content and/or user data with known characteristics or features, such as historical purchase data and/or past coupon data. Based on these analyses, the processing element may learn how to identify characteristics and patterns that may then be applied to analyzing user device details, user device sensors, geolocation information, image data, the retailer database, a third-party database, and/or other data. For example, the processing element may learn the fastest or easiest way to retrieve a coupon or how to extract relevant data from the coupon. Using the same example, the processing element may learn how to direct an OCR component where to extract the necessary data from a coupon.

VI. Additional Considerations

Although the above text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a processor or other programmable processor) that may be temporarily configured by software to perform certain operations. It should be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a processor configured using software, the processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment, or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed:

1. A computing system:
one or more processors; and
one or more computer memories storing non-transitory computer-executable instructions that, when executed via the one or more processors, cause the computing system to:
transmit a request for a server to generate and provide one or more available coupons as a portable document format (PDF) file or webpage representing the one or more available coupons;
obtain the generated PDF or webpage from the third-party server;
extract relevant coupon data for the one or more available coupons from the obtained PDF or webpage at least by (1) identifying an electronic file format of the obtained PDF or webpage, (2) standardizing or resizing the downloaded PDF or webpage based upon a pixel width of the downloaded PDF or webpage, (3) determining a pixel location of a bounding box containing the relevant coupon data within the standardized or resized PDF or webpage, and (4) applying an optical character recognition technique within the determined bounding box to identify text corresponding to the relevant coupon data; and
using the extracted relevant coupon data, apply the one or more available coupons in relation to a purchase of one or more products.

2. The computing system of claim 1, wherein the one or more products comprise one or more prescription medications.

3. The computing system of claim 1, wherein the non-transitory computer-executable instructions, when executed via the one or more processors, further cause the computing system to analyze a request from a user to purchase the one or more products, to determine whether the request qualifies for the one or more available coupons.

4. The computing system of claim 3, wherein determining whether the request qualifies for the one or more available coupons includes determining whether a user requesting to purchase the one or more products satisfies one or more criteria.

5. The computing system of claim 3, wherein the non-transitory computer-executable instructions, when executed via the one or more processors, further cause the computing system to update the request to purchase the one or more products after applying the one or more available coupons in order to adjust a price of the one or more products.

6. The computing system of claim 1, further comprising a clock component configured to define a frequency with which the computing system communicates with the server to identify available coupons.

7. The computing system of claim 1, wherein the relevant coupon data comprises a barcode.

8. A computer-implemented method implemented via one or more processors, the method comprising:
transmitting a request for a server to generate and provide one or more available coupons as a portable document format (PDF) file or webpage representing the one or more available coupons;
obtaining the generated PDF or webpage from the third-party server;
extracting relevant coupon data for the one or more available coupons from the obtained PDF or webpage at least by (1) identifying an electronic file format of the obtained PDF or webpage, (2) standardizing or resizing the downloaded PDF or webpage based upon a pixel width of the downloaded PDF or webpage, (3) determining a pixel location of a bounding box containing the relevant coupon data within the standardized or resized PDF or webpage, and (4) applying an optical character recognition technique within the determined bounding box to identify text corresponding to the relevant coupon data; and
using the extracted relevant coupon data, applying the one or more available coupons in relation to a purchase of one or more products.

9. The computer-implemented method of claim 8, wherein the one or more products comprise one or more prescription medications.

10. The computer-implemented method of claim 8, further comprising analyzing a request from a user to purchase the one or more products, to determine whether the request qualifies for the one or more available coupon.

11. The computer-implemented method of claim 10, wherein determining whether the request qualifies for the one or more available coupons includes determining whether a user requesting to purchase the one or more products satisfies one or more criteria.

12. The computer-implemented method of claim 10, further comprising updating the request to purchase the one or more products after applying the one or more available coupons in order to adjust a price of the one or more products.

13. The computer-implemented method of claim 8, comprising communicating with the server at pre-determined time intervals based upon a frequency defined by a clock component.

14. The computer-implemented method of claim 8, wherein the relevant coupon data comprises a barcode.

15. One or more non-transitory computer-readable media storing non-transitory computer-executable instructions that, when executed via one or more processors of one or more computers, cause the one or more computers to:
transmit a request for a server to generate and provide one or more available coupons as a portable document format (PDF) file or webpage representing the one or more available coupons;
obtain the generated PDF or webpage from the third-party server;
extract relevant coupon data for the one or more available coupons from the obtained PDF or webpage at least by (1) identifying an electronic file format of the obtained PDF or webpage, (2) standardizing or resizing the downloaded PDF or webpage based upon a pixel width of the downloaded PDF or webpage, (3) determining a pixel location of a bounding box containing the relevant coupon data within the standardized or resized PDF or webpage, and (4) applying an optical character recognition technique within the determined bounding box to identify text corresponding to the relevant coupon data; and
using the extracted relevant coupon data, apply the one or more available coupons in relation to a purchase of one or more products.

16. The one or more non-transitory computer-readable media of claim 15, wherein the one or more products comprise one or more prescription medications.

17. The one or more non-transitory computer-readable media of claim 15, wherein the non-transitory computer-executable instructions, when executed via the one or more processors, further cause the one or more computers to analyze a request from a user to purchase the one or more products, to determine whether the request qualifies for the one or more available coupons.

18. The one or more non-transitory computer-readable media of claim 17, wherein determining whether the request qualifies for the one or more available coupons includes determining whether a user requesting to purchase the one or more products satisfies one or more criteria.

19. The one or more non-transitory computer-readable media of claim 17, wherein the non-transitory computer-executable instructions, when executed via the one or more processors, further cause the one or more computers to update the request to purchase the one or more products after applying the one or more available coupons in order to adjust a price of the one or more products.

20. The one or more non-transitory computer-readable media of claim 15, wherein the non-transitory computer-executable instructions, when executed via the one or more processors, further cause the one or more computers to utilize a clock component to communicate with the server at pre-determined time intervals based upon a frequency defined by the clock component.

* * * * *